(12) United States Patent
Lewkowicz et al.

(10) Patent No.: US 8,672,863 B2
(45) Date of Patent: Mar. 18, 2014

(54) DEVICE AND METHOD FOR EXAMINING A BODY LUMEN

(75) Inventors: Shlomo Lewkowicz, Kiryat Tivon (IL); Daniel Gat, Haifa (IL); Yehudit Kraizer, Kiryat Tivon (IL); Zvika Gilad, Haifa (IL); David Leuw, Haifa (IL); Gavriel Meron, Petach Tikva (IL); Arkady Glukhovsky, Santa Clarita, CA (US); Howard D. Manten, Miami, FL (US)

(73) Assignee: Given Imaging Ltd., Yoqneam (IL)

( * ) Notice: Subject to any disclaimer, the term of this patent is extended or adjusted under 35 U.S.C. 154(b) by 581 days.

(21) Appl. No.: 12/687,692

(22) Filed: Jan. 14, 2010

(65) Prior Publication Data

US 2010/0121225 A1      May 13, 2010

Related U.S. Application Data

(63) Continuation of application No. 11/186,836, filed on Jul. 22, 2005, now abandoned, which is a continuation of application No. 10/192,861, filed on Jul. 11, 2002, now Pat. No. 7,083,578.

(30) Foreign Application Priority Data

Jul. 12, 2001    (IL) .......................... 144296
Dec. 16, 2001   (IL) .......................... 147126

(51) Int. Cl.
  *A61B 5/103*    (2006.01)
  *A61B 5/117*    (2006.01)

(52) U.S. Cl.
  USPC ...................................................... 600/593

(58) Field of Classification Search
  USPC .............. 600/587, 593, 101, 160, 167, 178; 424/463, 464, 466, 468, 470, 400, 424/451–453, 501, 426, 78.35, 78.37, 472, 424/457; 348/207, 294, 76, 65; 359/642; 521/99, 142, 149, 136, 134, 186, 189
  See application file for complete search history.

(56) References Cited

U.S. PATENT DOCUMENTS 3,719,183 A    3/1973   Schwartz
3,971,362 A    7/1976   Pope et al.

(Continued)

FOREIGN PATENT DOCUMENTS

DE    34 40 177     5/1986
DE    10018341      4/2000

(Continued)

OTHER PUBLICATIONS

The Radio Pill, Rowlands, et al., British Communications and Electronics, Aug. 1960, pp. 598-601.

(Continued)

*Primary Examiner* — Brian Szmal
(74) *Attorney, Agent, or Firm* — Pearl Cohen Zedek Latzer Baratz LLP

(57) ABSTRACT

A system and method for indicating transferability of a non-dissolvable target in-vivo device through the GI tract are described. The in vivo system includes a dissolvable in-vivo device which has two operational phases; an initial phase in which the device is of initial dimensions and a final phase in which the device is of final dimensions. In the initial phase the device can pass freely through a normally configured body lumen whereas it may not be able to pass freely through an abnormally configured lumen. In the final phase the device can pass freely through a body lumen even if it is abnormally configured.

15 Claims, 4 Drawing Sheets

(56) References Cited

U.S. PATENT DOCUMENTS

| | | |
|---|---|---|
| 4,177,800 A | 12/1979 | Enger |
| 4,239,040 A | 12/1980 | Hosoya et al. |
| 4,246,784 A | 1/1981 | Bowen |
| 4,278,077 A | 7/1981 | Mizumoto |
| 4,431,005 A | 2/1984 | McCormick |
| 4,439,197 A | 3/1984 | Honda et al. |
| 4,681,093 A | 7/1987 | Ono et al. |
| 4,689,621 A | 8/1987 | Kleinberg |
| 4,784,155 A | 11/1988 | Mills |
| 4,844,076 A | 7/1989 | Lesho et al. |
| 4,915,113 A | 4/1990 | Holman |
| 4,936,823 A | 6/1990 | Colvin et al. |
| 5,004,614 A | 4/1991 | Staniforth |
| 5,279,607 A | 1/1994 | Schentag et al. |
| 5,318,557 A | 6/1994 | Gross |
| 5,324,280 A | 6/1994 | Wong et al. |
| 5,330,427 A | 7/1994 | Weissenburger |
| 5,395,366 A | 3/1995 | D'Andrea et al. |
| 5,558,640 A | 9/1996 | Pfeiler et al. |
| 5,604,531 A | 2/1997 | Iddan et al. |
| 5,697,384 A | 12/1997 | Miyawaki et al. |
| 5,782,747 A | 7/1998 | Zimmon |
| 5,819,736 A | 10/1998 | Avny et al. |
| 5,906,579 A | 5/1999 | Vander Salm et al. |
| 5,972,389 A | 10/1999 | Shell et al. |
| 5,976,571 A | 11/1999 | Crison et al. |
| 5,993,378 A | 11/1999 | Lemelson |
| 6,172,640 B1 | 1/2001 | Durst et al. |
| 6,183,466 B1 | 2/2001 | Wong et al. |
| 6,188,355 B1 | 2/2001 | Gilboa |
| 6,240,312 B1 | 5/2001 | Alfano et al. |
| 6,346,269 B1 | 2/2002 | Hsiao et al. |
| 6,599,284 B2 | 7/2003 | Faour |
| 7,195,778 B2 | 3/2007 | Fleshner-Barak et al. |
| 2001/0035902 A1 | 11/2001 | Iddan et al. |
| 2001/0038831 A1 | 11/2001 | Park et al. |
| 2001/0045899 A1 | 11/2001 | Hoek |
| 2002/0103417 A1 | 8/2002 | Gazdzinski |
| 2002/0160043 A1 | 10/2002 | Coleman |
| 2002/0198470 A1 | 12/2002 | Imran et al. |
| 2003/0144570 A1 | 7/2003 | Hunter et al. |
| 2003/0167000 A1 | 9/2003 | Mullick et al. |
| 2003/0208107 A1 | 11/2003 | Refael |
| 2004/0066262 A1 | 4/2004 | Wenner |
| 2004/0176684 A1 | 9/2004 | Tabuchi et al. |
| 2006/0061472 A1 | 3/2006 | Lovoi et al. |
| 2006/0136051 A1 | 6/2006 | Furst et al. |

FOREIGN PATENT DOCUMENTS

| | | |
|---|---|---|
| DE | 10121191 | 4/2001 |
| EP | 0 344 770 | 12/1989 |
| JP | 4109927 | 4/1992 |
| JP | 1992-144533 | 5/1992 |
| JP | 5015515 | 1/1993 |
| JP | 6285044 | 10/1994 |
| JP | 2004520410 T | 7/2004 |
| WO | WO 88/00449 | 1/1988 |
| WO | WO 96/25877 | 8/1996 |
| WO | WO 99/61070 | 12/1999 |
| WO | WO 00/38655 | 7/2000 |
| WO | WO 01/50941 | 7/2001 |
| WO | WO 01/65995 | 9/2001 |
| WO | WO 01/78836 | 10/2001 |
| WO | WO 02/087493 | 11/2002 |
| WO | WO 03/005877 | 1/2003 |
| WO | WO 03/005951 | 1/2003 |

OTHER PUBLICATIONS

Wellesley company sends body monitors into space- Crum, Apr. 1998.
Wireless transmission of a color television moving image from the stomach using a miniature CCD camera, light source and microwave transmitter. Swain CP, Gong F, Mills TN. Gastrointest Endosc 1997; 45: AB40.
BBC News Online—Pill camera to 'broadcast from the gut' Feb. 21, 2000, www.news.bbc.co.uk.
W. Weitschies, R. Kotitz, D. Cordin, L. Trahms, High-Resolution Monitoring of Gastrointestinal Transit of Magnetically Marked Capsule, (1997), Journal of Pharmaceutical Sciences, vol. 86, No. 11, pp. 1218-1222.
Transit times for the Capsule Endoscope, Gastrointestinal Endoscopy 2001; 53 AB122.
International Search Report for International Application No. PCT/IL02/00562, dated Apr. 21, 2008.
Office Action for Australian Application No. 2008202321 dated Apr. 30, 2009.
European Search report of Application No. EP 05 07 7574, dated Jun. 19, 2006.
Office Action for U.S. Appl. No. 10/192,861 mailed on Oct. 19, 2004.
Office Action for U.S. Appl. No. 10/988,614 mailed on Apr. 7, 2009.
Office Action for U.S. Appl. No. 10/988,614 mailed on Oct. 28, 2008.
Office Action for U.S. Appl. No. 10/988,614 mailed on Mar. 27, 2008.
Office Action for U.S. Appl. No. 11/186,836 mailed on Mar. 18, 2008.
Office Action for U.S. Appl. No. 11/186,836 mailed on Sep. 11, 2008.
Office Action for U.S. Appl. No. 11/186,836 mailed on Mar. 13, 2009.
Office Action for European Patent Application No. 02 745 775.3 dated May 17, 2011.
Office Action for Japanese Patent Application No. 2005-323164 dated Mar. 8, 2011.
Supplementary Partial European Search Report for European Patent Application No. 02745775.3 dated Jan. 20, 2011.

DEVICE AND METHOD FOR EXAMINING A BODY LUMEN

CROSS-REFERENCE TO RELATED APPLICATIONS

This application is a continuation of U.S. patent application Ser. No. 11/186,836, entitled "Device and Method for Examining a Body Lumen", filed on Jul. 22, 2005 now abandoned, which is hereby incorporated by reference in its entirety, and which is a continuation of U.S. patent application Ser. No. 10/192,861, entitled "Device and Method for Examining a Body Lumen", filed on Jul. 11, 2002 now U.S. Pat. No. 7,083,578, which is hereby incorporated by reference in its entirety, and which claims priority and benefit from (a) Israeli Patent Application Number 144296, entitled "A Device and Method for Testing a Body Lumen Configuration", filed on Jul. 12, 2001, which is hereby incorporated by reference in its entirety, and (b) Israeli Patent Application Number 147126, entitled "A Device and Method for Testing a Body Lumen Configuration", filed on Dec. 16, 2001, which is hereby incorporated by reference in its entirety.

FIELD OF THE INVENTION

The present invention relates to a device and method for examining a body lumen. The device and method are useful, inter alia, in detecting abnormalities in a body lumen configuration.

BACKGROUND OF THE INVENTION

Tubular organs in the body may have a convoluted cavity configuration. The gastrointestinal tract, for example, starts from the oral cavity and proceeds through the esophagus, stomach, duodenum and small intestine, which is a long tube that folds many times to fit inside the abdomen. The small intestine is connected to the large intestine, which begins with the cecum, a small saclike evagination, then continues with the ascending colon, transverse colon, descending colon and the sigmoid (S-shaped) colon to the rectum. These body lumens may suffer from pathologies, which can affect the anatomy or configuration of the lumen. For example, strictures, narrowing or closure of a normally configured lumen can be caused by calcification or by the presence of scat tissue or a tumor. Structures of the esophagus are a common complication of chronic gastroeosophagaeal reflux disease (GERD). Acute, complete obstruction of the esophagus may occur when food is lodged in the esophageal stricture. Endoscopy is usually employed to retrieve the food and relieve the obstruction.

Several procedures are available for stretching (dilating) the strictures without having to resort to surgery. These involve placing a balloon or a dilator across the sticture during an endoscopy procedure.

Methods for diagnosis of body lumens are usually symptom related or invasive Non-invasive techniques of diagnosing the gastrointestinal (GI) tract include utilizing solid non-degradable swallowable autonomous electronic or magnetically marked capsules. These autonomous capsules include capsules for measuring motility in the GI tract, gastric pH (such as the Heidelberg capsule) and in vivo temperature (such as the CoreTemp™ capsule). Also, gastric transit may be measured by using biomagnetic measuring equipment such as a magnetically marked capsule, which is a solid non-degradable oral dosage form containing powdered magnetite encapsulated in silicone rubber (W. Weitschies, R. Kotitz, D. Cordin, L. Trahms, (1997), J Pharm Sci, 86:1218-1222). Such capsules are typically propelled through the GI system by peristalsis. These non-invasive methods enable reaching parts of the intestine, especially distal parts of the small intestine (jejunum and ileum) that cannot be reached by other methods. However, in rare cases of severe strictures in the GI tract, swallowing of a solid bolus (such as an electronic or magnetically marked capsule) may cause obstruction of the GI tract.

Also, drug delivery devices that are solid non-degradable boluses may often be swallowed. Drug delivery devices may include diffusion controlled systems or environmentally responsive systems. In these systems there may be a combination of polymer matrices and bio active agents (typically drugs) that allow for a drug to diffuse through the pores or macromolecular structure of the polymer upon introduction of the system in vivo. In some cases the devices are swelling-controlled release systems that are based on hydrogels. Hydrogels are polymers that will swell without dissolving when placed in water or other biological fluids. Thus, the swelling-controlled systems are initially dry and, when placed in the body, will absorb fluids and swell. The swelling increases the polymer mesh size enabling the drug to diffuse through the swollen network into the external environment. These systems are typically essentially stable in an in vivo environment and do not change their size either through swelling or degradation. The swallowing of these systems may thus, in cases of strictures in the GI tract, cause obstruction of the GI tract.

Non-invasive methods for detection of strictures, specifically in the GI tract, usually include x-ray series that are based on intake of x-ray opaque (radio-opaque) material (barium, gastrographine, or others). The material resides for some time on the walls of the GI tract, enabling examination of the x-ray images of the GI tract. This technique has several drawbacks, namely, low detection rate and exposure to x-ray radiation.

In-vivo devices, pills, or other medical systems may need to pass through the GI tract. However, it may be difficult to predict if such devices, pills, or systems may achieve safe passage through the GI tract, short of actually attempting to pass the objects through the tract.

Therefore, there exists a need for an efficient and low-hazard method of examining a body lumen. Specifically, there exists a need for a safe and high performing method of detecting abnormalities in a body lumen, such as abnormal motility in the GI tract, strictures or other configurational abnormalities in body lumens. In addition, there exists a need to determine whether objects of a certain size and/or shape may pass safely through the GI tract.

SUMMARY OF THE INVENTION

Embodiments of the present invention provide a device and method for in vivo examination of a body lumen. In one embodiment of the invention, a safe and simple non-invasive tester and method of testing of a body lumen's configuration are provided. Also provided according to an embodiment of the invention are a device and method for detecting configurational abnormalities in body lumens. Configurational abnormalities may include clinical/anatomical abnormalities in body lumens, such as strictures in the GI tract According to another embodiment the invention provides a device and method for testing motility in the GI tract.

A method, according to an embodiment of the invention, for testing a body lumen may include the steps of a. introducing into the body lumen a device, having initial dimensions for a predetermined period and reduced dimensions after the predetermined period; and b. monitoring the device. The body lumen may be the GI tract and the device may be ingested. Typically the predetermined period is one hundred hours or more, however, other periods may also be included according to embodiments of the invention.

According to one embodiment the device comprises a permeable coating and a filling disposed within the coating. The filling is capable of absorbing fluid from the body lumen Typically, after the predetermined period, the filling swells enough to burst the coating.

According to one embodiment the initial dimensions may be a diameter of about 11 mm and the reduced dimensions may be a diameter of about 2-10 μm. Other dimensions are possible.

A method according to an embodiment of the invention may include the step of detecting a signal emanated from a monitoring device that is connected to the device. The monitoring device, according to an embodiment of the invention, is typically of smaller dimensions than the device initial dimensions. The monitoring device may be a passive device, such as, an electronic ID tag, a magnetized device or an acoustic device. According to an embodiment of the invention a passive monitoring device may be monitored by detecting a signal that is emanated from the monitoring device. Detecting an emanated signal may be done, according to one embodiment, by generating an electromagnetic field to induce an induction power field having a first frequency and then receiving a signal having a second frequency from the monitoring unit. The signal having a second frequency may be an electromagnetic signal or an acoustic signal. Other signals may be detected.

According to another embodiment the monitoring device actively emits signals, such as electromagnetic or acoustic signals. According to yet a further embodiment the device includes a tag, such as radioactive material, magnetized particles or a radio opaque material. These tags may be detected by, for example, a radioactive emission detector, a magnometer or an x-ray machine. According to yet another embodiment the device includes a marker, such as a dye.

According to an embodiment of the invention a body lumen may be tested by utilizing a device that comprises a dissolvable body, a dissolvable plug affixed to the body, the body and plug defining a closed receptacle, and an essentially impermeable outer coating enclosing the plug and body The coating typically covers less than the entire plug. The device according to an embodiment of the invention may contain a tag, RFID, marker or any substance enclosed within the closed receptacle. According to certain embodiments of the invention after the predetermined period the body and plug are dissolved and the outer coating is depleted.

According to yet other embodiments the method may also include sensing at least one parameter of the body lumen, such as, pH, pressure and temperature. According to one embodiment data of the sensed parameter may be transmitted to an external receiving system.

According to an embodiment of the invention there is provided a method for sensing a subject's GI tract. The method includes ingesting an in vivo sensing device which comprising a sensor, a transmitter for transmitting sensed data and an electronic ID tag. According to one embodiment the sensor may be an image sensor Also provided, according to an embodiment of the invention is a method for controlled release of at least one substance in a configurationally or clinically abnormal GI tract. The method according to an embodiment of the invention includes ingesting a device, which includes a substance and comprises a dissolvable body, a dissolvable plug affixed to the body, the body and plug defining a closed receptacle, and an essentially impermeable outer coating enclosing the plug and body. The coating typically covers less than the entire plug According to one embodiment, at least one substance may be dispersed within the plug and at least one substance may be enclosed in the receptacle According to a further embodiment of the invention there is provided an in vivo imaging device comprising an image sensor, an illumination source, an internal power source and an electronic ID tag. The imaging device may also include a transmitter for transmitting image data to an external receiving system.

BRIEF DESCRIPTION OF THE FIGURES

The present invention will be understood and appreciated more fully from the following detailed description taken in conjunction with the drawings in which.

DETAILED DESCRIPTION OF THE INVENTION

Figure 1A:
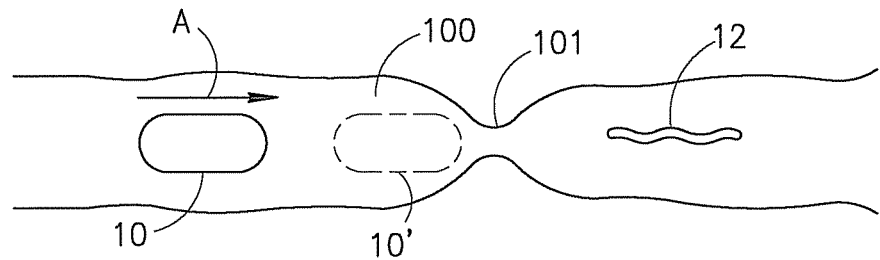
FIG. 1A is a schematic illustration of the two phases of an examining device in vivo, according to an embodiment of the invention.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

An atypical passage of an object through a body lumen or symptoms appearing after the insertion of an object into a body lumen may be indicative of an abnormal configuration of the body lumen. An examining device according to embodiments of the invention, which can examine a body lumen and can be an indicator of the body lumen configuration, is designed to be safely exited from the body, independently of the configuration of the body lumen.

According to an embodiment of the invention a device comprises a coating and a filling. The coating has initial dimensions that are changeable to final dimensions and the filling comprises particles that are of final dimensions. Final dimensions enable passage of the device in a body lumen configuration that is not enabled by the initial dimensions.

At a predetermined time a predetermined pressure, produced internally in the device, is exerted on the coating. The predetermined pressure causes the coating to rupture or collapse. Thus, at a predetermined time, the device is degraded or reduced, essentially in a step-wise manner, into dimensions that enable passage of the device in a body lumen configuration that is not enabled by the initial dimensions.

The predetermined pressure is typically unequal to the normally prevailing endo-luminal pressure. The predetermined time is a period greater than the period it typically takes for the device to pass through a normally configured body lumen.

The initial dimensions are typically determined in accordance with the known anatomy and/or physiology of a body lumen. In its final phase the dimensions of the examining device are typically smaller and its shape possibly changed such that it can freely pass through the body lumen even if the lumen dimensions are smaller than expected in accordance with the known anatomy and/or physiology of the body lumen.

Proceeding from an initial phase to a final phase of the examining device, namely by producing a predetermined pressure within the device, may, for example, be promoted by endo-luminal conditions or may be externally controlled. It should be appreciated that the device typically proceeds from an initial phase to a final phase, e.g. going through a change in dimensions, when the predetermined pressure is exerted on the device coating. The predetermined pressure is typically produced in the device and exerted on the device coating in vivo. It is therefore conceivable that a device according to an embodiment of the invention will remain in its initial phase indefinitely. For example, if the device is not inserted in vivo or if the device is inserted in vivo but is exited from the body within a time period that is shorter than the predetermined time, the predetermined pressure will not be produced in the device and the device will not go through a change of dimensions.

The examining device may further comprise a monitoring mechanism, such as a radioactive, color or magnetic tag or an electronic ID tag (e.g., an RFID tag). Other monitoring mechanisms may be used. An external operator, who can typically be advised of the phase the device is in at a given moment (as will be detailed below) may thus follow the progression of the device through the body lumen. Additionally, the device may also comprise an examining mechanism, such as a thermometer or pH meter, for examining endo-luminal conditions, or other sensing devices such as an imaging device.

In an embodiment of the invention the examining device is a testing device that comprises initial dimensions that will enable free passage of the testing device through a normally configured body lumen but not enable free passage of the testing device through certain strictured or otherwise narrowed or abnormally configured body lumens. In its final phase the size of the testing device is typically smaller and its shape possibly changed such that it can freely pass through the body lumen even if the lumen is abnormally configured.

In another embodiment of the invention the testing device may be used to simulate the passage of an in vivo device, such as a diagnostic and/or therapeutic device, through a body lumen. In this case, obtaining information on the passage of the testing device through the body lumen can be advantageous in designing a specific in vivo device or in determining whether a certain in vivo device may be safely used on a patient. In one embodiment, different sized and shaped testing devices according to an embodiment of the invention may be passed through a body lumen to determine the most suitable size and shape for an in vivo device to be freely and safely passed through this same lumen. In another embodiment the testing device comprises at least two phases, an initial phase in which the testing devices dimensions approximately resemble the dimensions of a target in vivo device and a final phase in which the dimensions of the testing device are changed so as to enable the testing device to pass through certain abnormally configured body lumens. Passing of the testing device through a body lumen simulates the passage of the target in vivo device through that body lumen and thus a safe method of indication is provided as to the transferability of the target in vivo device in the body lumen.

In the method according to an embodiment of the invention an examining device can examine endo-luminal conditions, or test the configuration of a body lumen, detect configurational abnormalities in a body lumen and/or simulate the passage of an in vivo device in a body lumen while posing no danger of long term obstruction of the body lumen. An examining device according to an embodiment of the invention in its initial phase comprises dimensions such that it can typically pass through a body lumen and/or give a good approximation of the passage of an in vivo device in the body lumen. In its final phase the examining device's dimensions may be changed (typically reduced, although other changes are contemplated) so that it can pass through an abnormally configured body lumen where the examining device in its initial phase could not, because of its dimensions.

In case the body lumen is of unexpected dimensions (wherein the expected dimensions are based, for example on the known or typical anatomy and/or physiology of the body lumen) or in case of a stricture or any other configurational abnormality in the body lumen, the examining device in its initial dimensions may be blocked from continuing its typical or expected passage in the body lumen. After a predetermined time the examining device's dimensions may be changed such that the testing device, in its final phase, typically of degraded or reduced form, will not be blocked from passing even through a smaller or abnormally configured body lumen.

If no clinical or configurational abnormalities are present in the body lumen the examining device's passage through the body lumen will be typical and the examining device passes through the body lumen and exits the body while it is still in its initial dimensions However, in a case in which the body lumen is abnormally configured (e.g., there is a stricture) or if there is a clinical problem (e g., slow or no motility in the GI tract) the examining device is held back in the body lumen and reaches its final dimensions while in the body lumen. The degraded or reduced device is able to continue its passage through the body lumen to eventually exit the body. It will thus be appreciated that the device and method of the invention can be utilized to detect clinical and/or configurational abnormalities in body lumens through which the device can be passed and exited, such as the GI tract, the urogenital tract, the reproductive tract, the oral-nasal cavity, etc, or a portion of any of these lumens.

A person skilled in the art can easily adjust the specific design of the examining device and the predetermined time period between an initial and final phase of the examining device to be applicable to a specific body lumen having specific and known anatomy and physiology.

Figure 1B:
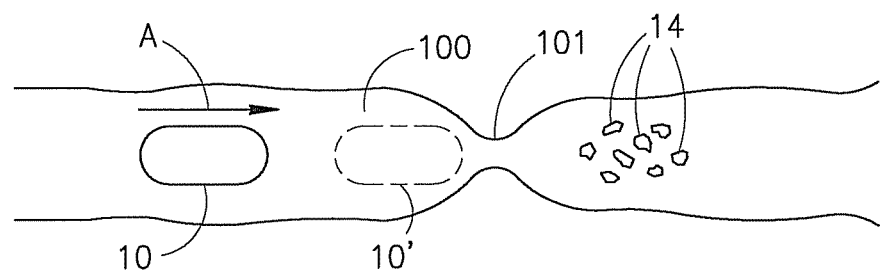
FIG. 1B is a schematic illustration of the two phases of an examining device in vivo, according to another embodiment of the invention.

FIGS. 1A and 1B are schematic illustrations of one embodiment of the invention. Referring to FIGS. 1A and 1B, an examining device 10, having initial dimensions, is inserted into a body lumen 100 and is moved through the body lumen 100 (in the direction indicated by the arrow A) either actively or passively. The device 10, which has a diameter of, for example, 1-12 mm, can pass freely through the lumen 100 that spans over a width of, for example, 1 mm to 10 cm, until a stricture 101 is reached. At the stricture 101, there is only a residual functioning lumen of, for example, about 2-10 μm. The device (now illustrated in a broken line and referred to by the numeral 10') is unable to continue its passage through the body lumen 100 due to its dimensions, which are larger than the dimensions of the body lumen at the stricture 101. The device 10, in its initial dimensions, is thus blocked at the stricture 101.

After a predetermined time the device's 10 dimensions are changed. The device 10 can be, for example, collapsed or disintegrated resulting in its final dimensions 12 (in FIG. 1A) or ruptured or degraded, resulting in its final dimensions 14 (in FIG. 1B). In its final dimensions 12 the device typically has reduced volume and a flattened shape, its diameter no more than, for example, 2-10 .mu.m. In its final dimensions 14 the device may be, for example, degraded into several small sections or particles, each of which is no more than, for example, 2 .mu.m wide. The device in its final dimensions either 12 or 14 can pass through the stricture 101 and can be existed from the body. In alternate embodiments, the dimensions or shape of the body lumen 100 may be different and the device 10 may be changed in other manners, to other dimensions or shapes For example, the device need not be broken into more than one section.

The examining device 10 can be, for example, capsule shaped, similar to the swallowable capsule described in U.S. Pat. No. 5,604,531 to Iddan (which is hereby incorporated by reference) or similar in shape and size to other pills, tables capsules and the like, known in the art.

In one embodiment, a capsule shaped testing device having initial dimensions of approximately 11 mm.times.26 mm can be used to test the GI tract. The device is swallowed or otherwise placed in the GI tract (by an endoscope, for example) and is passively moved through the GI tract due to peristalsis of the GI tract, until it is naturally excreted from the body. Alternatively, the device may be moved through the body lumen by an external operator by means such as an endoscope, needle, stent etc. Should the device be unable to move past a certain point, due to the body lumen configuration at that point the device will be left at that point and will be degraded after a predetermined time. After the device is degraded or reduced, for example as shown in FIGS. 1A and 1B, it will be naturally excreted from the body lumen.

Also, in one embodiment, a powerful magnet can be used from the outside of the body to move a charged device within the body lumen. Should the external operator be unable to move the device past a certain point, due to the body lumen configuration at that point, the device can be left at that point and it will be degraded after a predetermined time. After the device is degraded or reduced, for example as shown in FIGS. 1A and 1B, it is able to passively and naturally exit the body lumen.

In another embodiment the device 10 may be shaped or sized to resemble a target diagnostic or therapeutic device, which itself is desired to be passed through the patient's body lumen, for example, a swallowable imaging device for purposes of imaging the GI tract. The device 10 can be safely passed through the GI tract, to test the transferability of such a device through the GI tract, while its progression can be monitored and/or the phase the device is in can be detected (as will be further detailed below). In the event the device cannot traverse a section of the lumen, its shape or dimensions may change to allow passage.

Figure 2A:
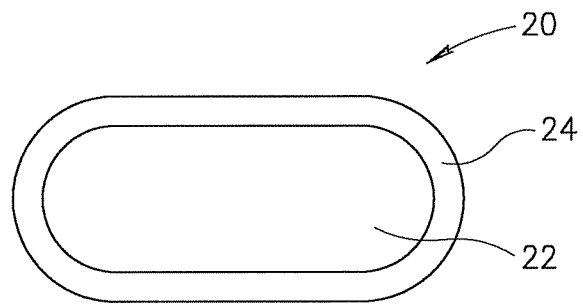
FIG. 2A is a schematic cross section illustration of an examining device having a coating and a filling, in accordance with an embodiment of the invention.
Figure 2B:
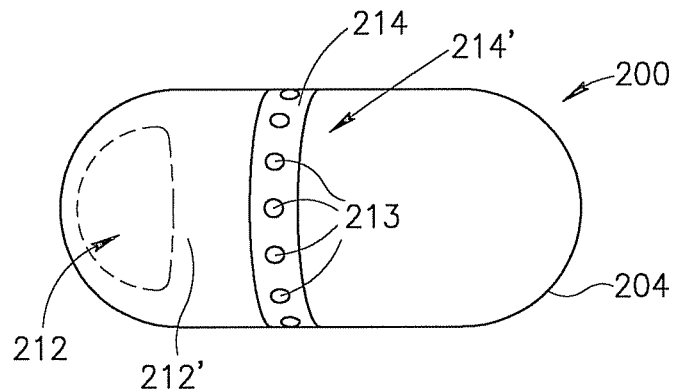
FIG. 2B is a schematic side view illustration of an examining device having a coating and a filling a in accordance with another embodiment of the invention.

Test devices according to several embodiments of the invention are schematically illustrated in FIGS. 2A and 2B, however other embodiments of devices having other shapes, dimensions and structures may also be used. According to one embodiment of the invention, a test device is made of an outer coating and internal filling. Test devices for the GI tact, for example, may initially have an outer coating and internal filling each of, for example, a few μm to a few mm thick. Typically, the outer coating is a thinner layer than the internal filling. According to some embodiments, the outer coating is designed to impart mechanical strength to the device and keep the device shape and dimensions constant throughout the initial phase of the device. The coating also serves as a barrier between the internal filling and the surrounding, such as, the endo-luminal environment. The coating is typically a layer or a plurality of layers of imperimeable or slightly permeable material or combination of materials, that is essentially durable (i.e., does not corrode or disintegrate) under in vivo conditions, The internal filling, which in one embodiment can be one or more layers or a suspension or liquid or gas, typically constitutes small particles or molecules and can produce pressure within the device by, for example, serving as an ion source or sink. The filling may also contain adhesives and fillers to, for example, further provide mechanical stability to the device.

Referring to FIG. 2A, the test device 20 according to one embodiment comprises an outer coating 24 and an internal filling 22. The outer coating 24 is a layer of strong, slightly permeable material which encapsulates the internal filling 22 and controls the diffusion rate of substances from within the device and/or from the outside (e.g. the body lumen environment) into the device. The internal filling 22 maintains an osmolarity that favors the inward or outward diffusion of ions, such that the internal filling will swell or be depleted (and exchanged for endo-luminal liquids) in a process which will preferably be determined by the properties of the internal filling 22 and the late of which will be preferably limited by the properties of the outer coating 24.

In one embodiment the outer coating 24 may be made of a Parylene C coated hydrogel polymer, such as ethyl cellulose acetate and the internal filling 22 may be made of filler, preferably a biodegradable polymer, such as polymer of lactide and golycollide (PLGA). In alternate embodiments, other materials may be used. Parylene C, which is a dimer of poly p-xylene with a substitution of a single chlorine molecule, provides a combination of properties such as a low permeability to moisture, chemicals, and other corrosive gases. The hydrogel polymer creates a matrix that contains the filler and that is strong enough to withstand endo-luminal pressure. The filler absorbs liquid from the body lumen environment which seeps through the hydrogel matrix at a rate which is typically determined by the osmotic gradient between the endo-luminal environment and the inner filling and by properties of the Parylene C coating and of the hydrogel polymer, such as by the extent of the hydrogel polymer cross linking, its concentration, its thickness and so on.

The filler swells and after a period of time, starts pressing against the outer coating 24. The internal pressure rises as more liquid is absorbed. When the pressure reaches a certain, predetermined point the hydrogel matrix and the Parylene C coating rupture and the device 20 is separate into smaller pieces and particles.

In another embodiment, the outer coating 24 may be a low solubility material that is permissive to an inward flow of endo-luminal liquids or a soluble material that is initially impermeable to endo-luminal liquids but becomes permeable as it is dissolved, due to thinning of the layer. The inward flow of endo-luminal liquids causes the pressure in the device 20 to be elevated and ultimately the outer coating 24 is ruptured, thereby diminishing the dimensions of the device 20.

For example, in a device having a diameter of 11 mm, a layer of Parylene C, a few μm thick (5-20 μm) can be used as the outer coating 24 and a 11 mm thick filling of any suitable filler can be used as the internal filling 22. The thickness of the outer coating layer serves to regulate the rate of the inward flow of endo-luminal liquids. In another embodiment the outer coating 24 can be made of a 10 .mu.m thick layer of Parylene C and a 0.5 mm thick layer- of gelatin. The gelatin, which may be soft, hard or vegetable gelatin, may be cross-linked to increase its durability. Thus, a device comprising an outer layer made of Parylene C may be designed to go through a change in dimensions at a desired rate. Of course, other dimensions, and other suitable substances, may be used.

The device 20 can be manufactured to be of a shape that is similar to pharmaceutical tablets, pills, capsules etc, by molding, pressing, extruding and so on. For example, the internal filling 22, which may include microspheres of a hydrophilic substance encapsulated within a fatty based matrix or within a coating of Parylene C, may be pressed into a tablet about 11 mm thick, and then coated by a thin (about 10 μm), outer coating 24 that, typically, is not degradable under endo-luminal conditions (such as low pH, temperature, enzymatic degradation etc.). When in use, the microshperes absorb liquids from the environment and swell, building up pressure ultimately causing the outer coating 24 to rupture.

In an alternative embodiment the osmolarity of the internal filling may favor a diffusion of ions into the body lumen, a gradual depletion of the internal core and a flow of liquids into the device. The depleting internal core is exchanged for liquids, which exert pressure on the device coating, and after a predetermined point the outer coating is ruptured and the entire device is diminished.

It should be appreciated that the device may comprise more than two layers, each layer having its own dynamics, as described above. Further, it should be appreciated that the change in dimension of the device can be influenced by different parameters, such as by the thickness of each layer or by different properties of the material fabricating each layer etc. A predetermined pressure that is suitable for rupturing one coating may be unsuitable for rupturing another coating. For example, different hydrogel fillings can be induced to go through a change of swelling. A thermo-responsive hydrogel can be stimulated by a change in temperature to go through polymer-polymer and water-polymer interactions, which results in a change in swelling of the hydrogel. Likewise, an acidic or basic hydrogel will be induced by a change in pH. The swelling of modified hydrogels can also be stimulated. For example, a hydrogel containing electron accepting groups will be stimulated by the presence of electron donating compounds, a poly electrolyte hydrogel will be stimulated in the presence of an applied electric field and magnetic particles dispersed in microspheres, such as alginate microspheres, will be stimulated in the presence of an applied magnetic field. Thus, a device according to an embodiment of the invention may be externally controlled, namely, the transition of the device from an initial phase to a final phase can be controlled, for example, by artificially changing the endo-luminal temperature or pH or by externally applying an electric or magnetic field to the body lumen.

External control of the transition of the device from an initial phase to a final phase may be useful in cases in which the device is blocked in a body lumen having an environment that does not favor the transition from an initial phase to a final phase. For example, the device may be blocked in a patient's large intestine due to a stricture in the large intestine. The endo-luminal environment in the large intestine might, at times, not be diluted enough to provide the predetermined pressure by an inward flow of endo-luminal liquids. The transition of the device to its final dimensions may then be initiated externally, for example, as described above, in order to contribute to the diminishing of the device.

It should be appreciated that the device according to an embodiment of the invention can be made of materials that are degradable by external methods such as by ultrasound, in case an external operator wishes to diminish the device before that device is changed to its final dimensions.

In FIG. 2B the device 200 comprises an outer coating 204 and an inner filler (not shown). The outer coating 204 is differentially strengthened, i.e., having areas of different strengths. Device 200 can be, for example, capsule shaped or otherwise shaped. The outer coating 204 and inner filler can be made of any suitable material, for example, as discussed above. Specific areas in the outer coating 204 are weaker than neighboring areas such that when pressure is exerted on these weaker areas, the outer coating 204 breaks or collapses in the vicinity of these areas. In the example illustrated in FIG. 2B, a patch 212 at one end of the device 200 or a band 214 around the middle of the device 200 are weaker than neighboring areas 212' and 214'. For example, patch 212 and/or band 214 may be thinner than neighboring areas and will thus are more susceptible to pressure than the neighboring areas 212' and 214'. Alternatively, patch 212 and/or band 214 can be more permeable to liquids than neighboring areas and thus, while in a body lumen, a larger flow of endo-luminal liquids pass through these areas than through neighboring areas. This differential flow of liquids causes pressure to be exerted in the vicinity of the more permeable areas, thereby causing the outer coating 204 to break or collapse in these areas. Differential permeability in these areas can be caused by, for example, using a thinner layer of coating in these areas, by puncturing holes 213 in these areas, by using different materials to manufacture the different areas and so on.

A device 200 can include an outer coating 204 and an internal filler that is a body of gas or liquid. Alternatively, the device may include multiple layers; outer coating layers and internal filler layers, as described above. Pressure of a certain amount exerted by the in or out flow of liquids or by swelling of an internal core layer against the outer coating causes the outer coating 204 to break at specific weakened areas, such as at patch 212 and/or along band 214. Thus, device 200 having an outer coating 204 with areas of differential strength can be designed to go through a change of dimensions in a step-wise manner, wherein the breaking of the outer coating, which can be brought about gradually, will cause an immediate change of dimensions of device 200.

In such an embodiment, during the initial phase, while the pressure in the device is increasing, the outer coating is unaffected by the rising pressure or by endo-luminal conditions (even if there is erosion of the outer coating during the initial phase, it will typically be not more than about 5% of the initial outer coating dimensions) and thus, the device shape and dimensions are not significantly changed. However, once the predetermined pressure is achieved the outer coating will collapse or rupture and the device's dimensions will be reduced in a step-wise or an approximation of a step-wise manner Thus, although both outer coating and internal filling may change dimensions or dissolve gradually, the overall reaction is an approximation of a step function.

Figure 2C:
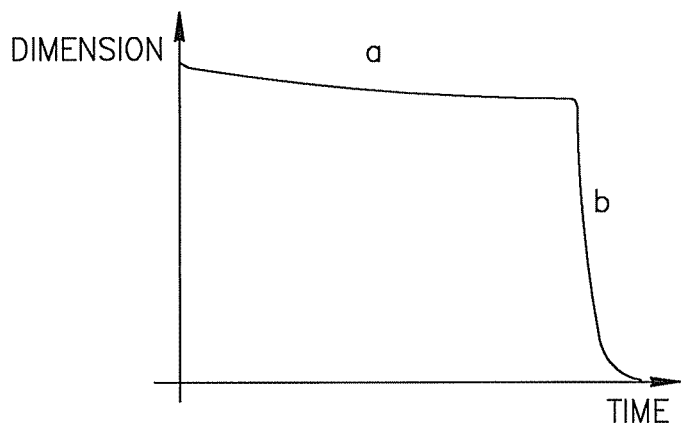
FIG. 2C is a graph illustrating the step function followed by the examining device according to an embodiment of the invention.

An approximation of a step-wise reaction, according to an embodiment of the invention, is schematically presented in FIG. 2C. The graph shown in FIG. 2C, which represents the dissolving of a two-layer device according to one embodiment, includes two exponents represented as (a) and (b). The first exponent (a) represents an outer layer with essentially fixed dimensions (e.g., a change of dimensions up to about 5% of the initial dimensions) while the second exponent (b) represents a depleting or dissolving inner layers The outer layer protects and prevents dissolving or depleting of the inner layer. However, once the outer layer is dissolved or ruptured the process of dissolving or depleting of the inner layer is initiated. The combination of the two exponents approximates the required step function.

A testing device is not always easily seen when it is in a person's body and it might not be known when the device exits the body, for example in the case of a testing device for the GI tract. A person having swallowed or otherwise ingested a test capsule does not always know when and in what dimensions the test capsule exited his body. In one embodiment, a test capsule for the GI tract is designed to stay in its initial dimensions, under in vivo conditions, for about 100 hours or more. In alternate embodiments, other time limits may be used, and testing devices for other body lumens may be designed in accordance with the specific body lumen having specific and known anatomy and physiology.

In another embodiment of the invention a monitoring mechanism is included, which enables a user to externally follow the progress of the testing device or otherwise track the testing device in the body lumen. Slowing down or blocking of the device in the body lumen, for a period that is longer than the time it typically takes for a device to pass through a normally configured lumen, implies an abnormality of the body lumen. The location of the testing device at a given moment in a body lumen can be determined by known methods. Thus, clinical abnormalities and/or conformational abnormalities, such as strictures in the GI tract, can be identified and localized to specific areas in the body lumen.

Figure 3A:
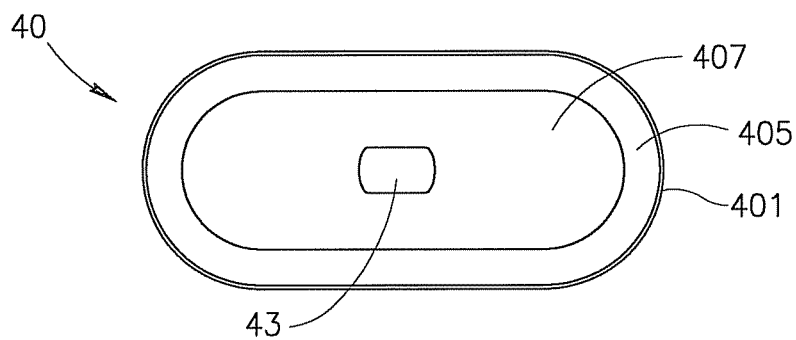
FIG. 3A is a schematic illustration of an examining device comprising a monitoring device in accordance with an embodiment of the invention.
Figure 3B:
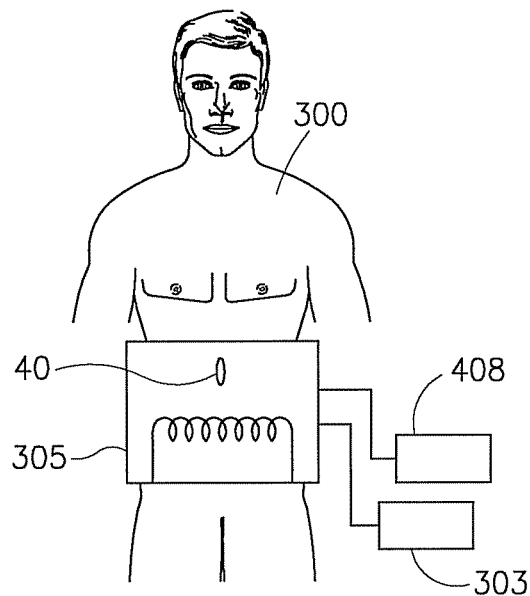
FIG. 3B is a schematic illustration of a monitoring system according to an embodiment of the invention.

Testing devices according to some embodiment of the invention are illustrated and exemplified in FIGS. 3A-3D. Referring to FIGS. 3A and 3B the testing device 40, which may be designed and fabricated as discussed above, includes, for example, a thin semi permeable rate limiting coating 401, such as a 10 .mu.m thick Parylene C coating, a thicker, mechanical stability imparting shell 405, such as a 1-2 mm thick layer of gelatin, a swellable filler 407, such as a 3-4 mm thick layer of a hydrogel and a monitoring device 43, which in one embodiment is approximately 3 mm wide. The device 40 is swallowed or otherwise inserted into the patient's 300 GI tract and the patient 300 is then monitored by being placed in the vicinity of a receiving system 305, as will be further detailed below.

The monitoring device 43 may be, for example, a passive ID tag, advising of its presence only upon external activation. Such an ID tag may be of known construction including, for example, a processor (not shown), a transmitter (not shown) and an antenna (not shown) to receive energy from an external transmitting device 303. Such miniature passive ID tags are used for example as implantable tags for animal identification. Such implantable tags are manufactured by Tiris, Microchip, and other companies.

In alternate embodiments, the tag may include other components; for example, the tag may include a Gunn diode instead of a processor. In another embodiment the tag may include a passive acoustic element that will respond to external induction by creating at least one acoustic signal, such as a squeak, beep or click. An external operator can induce the tag to send an acoustic signal and can then listen for the signal by putting a stethoscope, for example, to the patient's body. Hearing the signal will indicate that the tag is still in the patient's body. The operation of the tag can be coupled to the device such that if the device has disintegrated the tag will not respond by sending an acoustic signal. For example, a component of the tag, such as a battery for powering the tag, may be attached to the device shell such that when the device shell is ruptured or collapsed the battery will no longer be connected to the tag and the tag will not be able to produce an acoustic signal.

In another embodiment the monitoring device 43 is magnetized to obtain a net magnetic dipole moment. After the device 40 is introduced in vivo, its magnetic field distribution over the body lumen can be recorded for several time intervals with a receiving system 305 (e.g., a magnetometer) and at each time point the position of the device within the body lumen may be calculated from the measured field distribution, assuming a magnetic dipole model.

Optionally, the monitoring device 43 may be active, such as a beacon continuously or periodically signaling to an external receiving system 305, advising its presence. In one embodiment, the monitoring device 43 is an acoustic beacon. The acoustic beacon, according to an embodiment of the invention, generates at least one acoustic signal. According to another embodiment the acoustic beacon includes an electronic circuit that produces a periodic pulse (for example every 15-30 seconds). The circuit is connected to an acoustic element, such as a buzzer, clicker, beeper etc., for example via an electro-acoustic converter, so that an acoustic signal is periodically generated.

In one embodiment the monitoring device 43 is powered by a Power Paper™ power source provided by Power Paper Ltd., Israel. Preferably, the battery can last for over 200 hours. The monitoring device 43 may be operated by a read-relay switch. The switch can be turned to an ON of OFF position by distancing an external magnet from the monitoring device 43, as known in the art. Thus, for example, the device 40, which includes a monitoring device 43, such as an acoustic beacon, can be packaged in a magnetic package. The acoustic beacon is turned off while still in the magnetic packaging. Once the device 40 is released from the packaging, typically just prior to inserting the device 40 in vivo, the monitoring device 43 is activated. In another embodiment the acoustic beacon can be activated only after-device 40 has ruptured or disintegrated.

An external operator can, at any point after the device 40 has been inserted in vivo, listen for the acoustic signal by any known means, for example, by putting a stethoscope to the patient's body. Hearing the signal indicates that the tag is still in the patient's body. The approximate location of the monitoring device may be inferred In an alternative embodiment, signals from the monitoring device 43 are received by receiving system 305 and the location of the monitoring device 43 can be calculated by known triangulation methods. The calculations, according to an embodiment of the invention, are carried out on a processing unit 408 Thus, the monitoring device 43 can be monitored and its position can be known, while it is in the patient's 300 body and when it exits the patient's body.

The monitoring device 43, typically a miniature device, is shaped and sized such that it in itself can freely pass through a body lumen even if the body lumen is strictured or narrowed or otherwise abnormally configured. In such a case, the device 40 is ruptured or collapsed or otherwise altered as described above and the diminished device 40 and the monitoring device 43 pass freely through the body lumen to exit the patient's body.

Figure 3C:
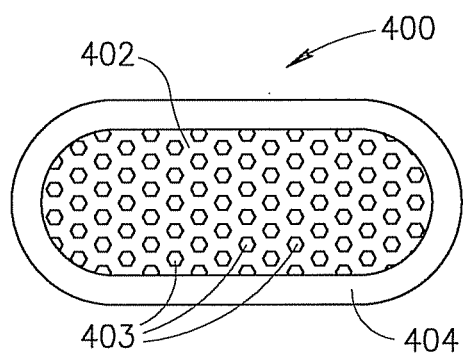
FIG. 3C is a schematic cross section illustration of a traceable examining device in accordance with another embodiment of the invention.
Figure 3D:
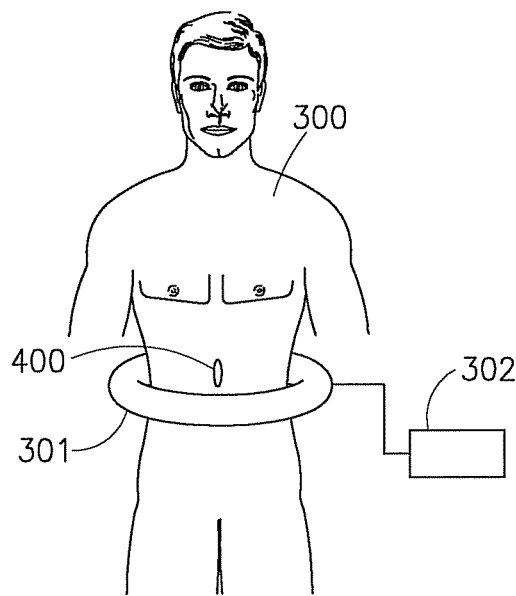
FIG. 3D is a schematic illustration of a monitoring system according to another embodiment of the invention.

Referring to FIGS. 3C and 3D, a testing device 400 in one embodiment comprises an outer coating 404 and an internal filling 402. The outer coating 404 and internal filling 402 can be fabricated as described above. The internal filling 402, which may be a filler, may further comprise a marker 403. In one embodiment the marker is radio opaque material, such as barium sulfate, or other detectable material, such that the testing device 400 can be viewed by x-ray or other detection methods In an alternative embodiment the marker is a dye, which can be dispersed or embedded in the filling In yet another embodiment the marker is magnetite (Fe3O4), for example, powdered magnetite in poly(methyl methacrylate). In this case the device 400 is magnetized to obtain a net magnetic dipole moment such that the device 400 can be monitored as described in reference to FIGS. 3A and 3B. Further, in yet another embodiment the marker is a radioactive marker. In another embodiment the marker may be a chemical that can interact with the patient's body to achieve a sensation that is felt by the patient. For example, niacin that is let to interact with the patient's body may cause sensation, advising the patient that the niacin has been released into his body.

The device 400 is inserted into a patient's 300 GI tract and can be monitored by a suitable detector 301, for example, an x-ray machine, a gamma camera or a magnetometer The detector 301 is typically moved along the patient's 300 body and utilizing a plurality of detectors or receivers (not shown) and a processing unit 302, can detect and calculate, by known methods, the location of the marker 403.

Typically, when the device 400 reaches its final dimensions the outer coating 404 is dissolved or ruptured and the internal filling 402 and any marker 403 dispersed or embedded therein, is released into the body lumen. Thus, according to one embodiment a patient 300 or an external operator can be advised of the fact that the device 400 has reached its final dimensions by a sudden sensation, for example or by the appearance of a marker in body lumen contents or excretions, for example by the appearance of colored stool, etc. In another embodiment of the invention a marker 403 can be used to mark the location of a stricture or other configurational abnormality. The marker 403, which may be a dye, can be dispersed or embedded within the internal filling or contained in a separate layer under the coating 404, to be exposed when the outer coating 404 is dissolved or ruptured. Thus, a marker can be let out in a lumen at the location of an abnormal configuration of that lumen (such as at the location of a stricture) and can consequently mark the location. In one embodiment a subject may swallow a device according to an embodiment of the invention, for testing the GI tract. In case of a stricture the device will be delayed at the stricture and eventually it will go through a change of dimensions, as described above, releasing a marker at the site of the stricture. A surgeon will then be able to identify the location of the stricture by externally viewing the GI tract and detecting the marker. The procedure of removing a stricture, for example, in the GI tract may thereby be facilitated. In another embodiment the device may also include a tag, such as the tags described above, for assisting in localizing the device.

In some embodiments it may be preferable that the marker be long lasting (for example, a few days) and visible through lumen tissues, so that it is detectable from the outside of the lumen. Examples of such markers can be Indian ink or known metal markers. Also, particularly for use in the GI tract, edible markers, such as food coloring, may be employed In an additional embodiment the marker may be sprayed out of the device, for example by producing high pressure in the layer that contains the marker, such that when this layer is exposed its contents are forcefully propelled from the device onto the nearby lumen tissue. Other methods of forcefully propelling the marker from the device may be possible, such as by employing an injecting mechanism in the device that is activated when the outer coating is dissolved or ruptured.

According to another embodiment, as long as the outer coating 404 is intact and the marker 403 is enclosed within the outer coating 404 the marker 403 will be detectable by the detector 301. If the outer coating 404 is dissolved or ruptured the internal filling 402 and any marker 403 dispersed or embedded therein will be released into the body lumen and dispersed such that the marker 403 will no longer be detectable by the detector, 301. Thus, the testing device 400 can be monitored while in its initial dimensions, by using detector 301. Once the device 400 reaches its final dimensions the marker 403 will be dispersed and undetectable by detector 301. The device 400 may thus be monitored and its position, while in the initial phase, can be calculated. In the final phase the filling will be dispersed in the body lumen environment such that the signal typical of the initial phase will no longer exist. Device 400 may also contain a monitoring device, such as the monitoring device 43 (FIG. 3A) for further monitoring after the device 400 reaches its final dimensions.

Additionally, monitoring device 43 may also serve as a platform for additional in vivo sensing units, such as a pH meter, a thermometer, an imager; a pressure detector etc. The sensing units may transmit data, wirelessly or not to an external receiving system while traversing the body lumen. Optionally, the devices according to embodiments of the invention may comprise a miniature in vivo sensing unit, as above, that is not connected to the monitoring device 43.

According to one embodiment an in vivo imaging device, such as the device described in WO 01/65995 (incorporated herein by reference) may include an electronic tag, such as an RFID. An imaging device, according to one embodiment may include an electronic tag, an image sensor, an illumination source and an internal power supply, such as a battery. The imaging device may also include a transmitter for transmitting image data to an external receiving system.

Figure 4:
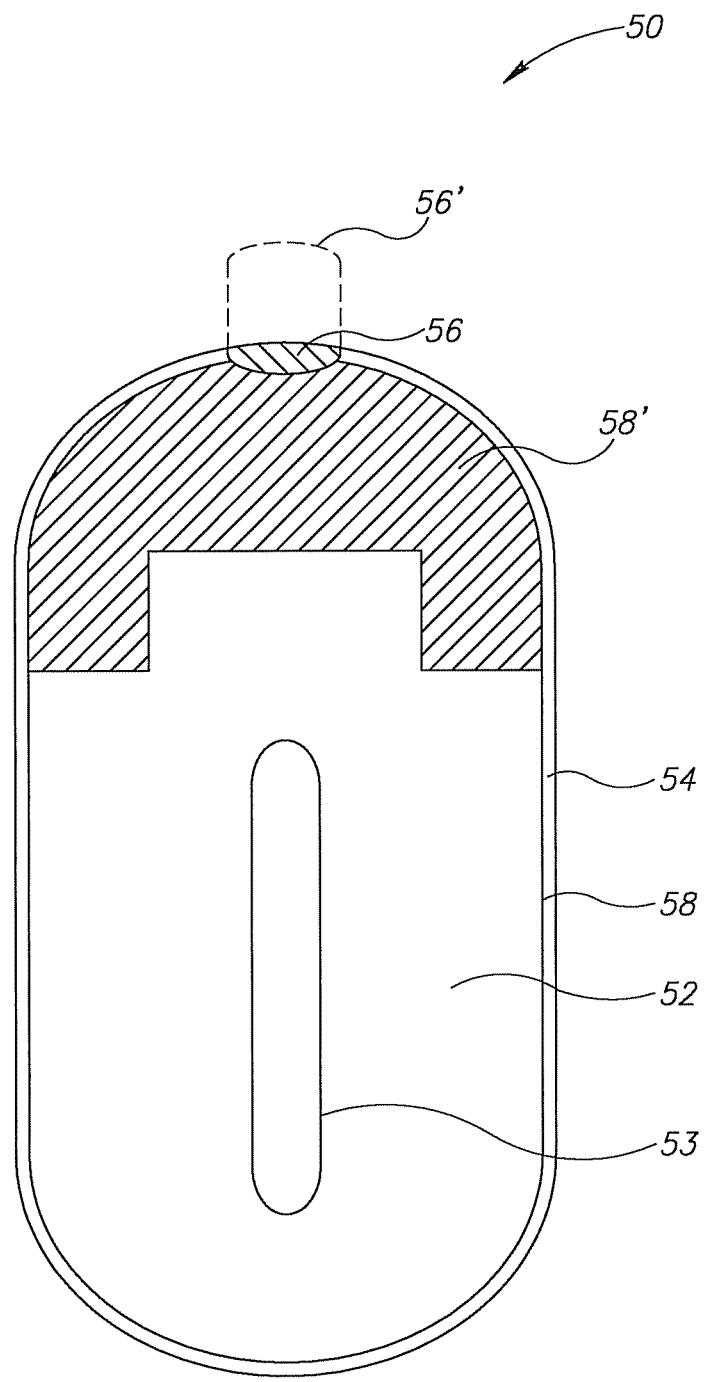
FIG. 4 is a schematic illustration of an examining device according to an embodiment of the invention.

Reference is now made to FIG. 4, which schematically illustrates an examining device according to one embodiment of the invention. Device 50 has a body 58 and a plug 58', which are typically but not necessarily made of different materials. The body 58 and plug 58' enclose an inner space which typically contains a filler 52 and an ID tag 53. The body 58 and plug 58' are coated by a thin coating layer 54, except at window 56. At window 56 the plug 58' may be exposed and come in direct contact with a body lumen environment. According to one embodiment, the device 50 can be assembled by affixing (for example by gluing) a filler and ID tag filled body to a plug having a protrusion 56'. The filler 52 filled body 58 with the protrusion 56' containing plug 58', fixed to it are then coated by coating layer 54 The protrusion 56' is then cut off close to the plug 58', leaving a window 56 that is not coated by coating layer 54.

Device 50 can be inserted into the GI tract and may be propelled through GI tract by, for example, peristalsis, as described above. The coating layer 54 is typically impermeable to GI tract liquids while the plug 58' is typically permeable to the GI tract liquids. Liquids from the environment may thus enter through window 56, which is unprotected by coating layer 54. GI tract liquids will diff-use or flow in through window 56, dissolving the plug 58', at a rate that can be dependant on parameters, such as, the size of window 56, the properties of the material fabricating plug 58' and the thickness of the plug 58'. After a predetermined time the plug 58' will dissolve enough to create an opening through window 56 through which GI tract liquids may come into contact with the body 58 and through which filler 52 and eventually, ID tag 53 may leave device 50. The body 58 is typically made of a material that is faster to dissolve than the material fabricating the plug 58'. Thus, once an opening is created in plug 58' the device 50 will be rapidly depleted of its contents leaving only an empty coating layer 54.

A device according to an embodiment of the invention may be made of, for example, a gelatin body and a wax plug. Other materials may be used. The device may be filled with powdered sugar into which a glass coated 12.times.2 mm RF ID tag (or other suitable identification or beacon device) is inserted. The filled body and plug may be coated by, for example, an 8-10 .mu.m layer of Parylene C. In alternate embodiments the plug may be made of, for example, lipophilic material of plant origin or hydrocarbons (simple and/or complex). According to an embodiment of the invention the plug may be made of essentially hydrophobic material, e.g., wax. According to one embodiment the hydrophobic material may comprise micro-particles to facilitate flow of body fluids into the plug and to facilitate the disintegration of the plug. A system that may be suitable to use in an embodiment of the present invention may be a system of nano-particles, for example, formed of a solid hydrophobic inner core and a cationic exterior. The nano-particles may be encapsulated in micro-capsules. In one embodiment the nano-particles may be encapsulated in moisture sensitive micro-capsules. Such systems are produced, for example, by Salvona, USA. The device may be filled with, for example, powdered sugar and other exepients. Barium or other, suitable material may be mixed into the filling for easily monitoring the device by x-ray. Alternatively, the device may not need a filling, which is usually intended to impart mechanical strength to the device. For example, the gelatin body may be thick enough to impart the required mechanical strength without being filled with a powder filling. The device containing the ID tag may be monitored by using a reader such as a suitable reader provided by Trovan Ltd. UK. The tag may be the tags described herein, such as a radioactive marker, a magnetic device, or a radio based tag.

In an alternative embodiment, a device, according to an embodiment of the invention may be utilized for controlled release of substances into a body lumen, such as the GI tract. According to an embodiment of the invention substances, such as an active agent, a medicament or markers may be included in a component or compartment of the device, to be released in a body lumen. In one embodiment the substances may be released at a specific site, typically at a site of an abnormal configuration, such as a stricture. According to one embodiment the filler 52 may include medicaments specifically intended to treat a strictured or constipated GI tract. Such medicaments may include, for example, steroids. For example, one or more active agents in powder form may be mixed with any suitable filler, for example, as described above. According to another embodiment one or more active agents may be included in a nano-particle that is microencapsulated in plug 58'. In yet another embodiment one or more active agents may be incorporated in body 58. The active agents may be soluble in the components of the plug 58' or the body 58 or the active agents may be dispersed in a solid matrix, for example, in material comprising body 58 or in the nano-particles that are included in the plug 58'. Similarly, a marker, as discussed above, may be incorporated into components of a device according to an embodiment of the invention. Medicaments or other substances may be inserted into the device in form of a tablet gel or liquid. According to one embodiment a liquid solution containing a substance may be an oily solution that does not dissolve the gelatin body. The incorporation of substances, such as active agents or markers, into components of the device, according to embodiments of the invention, may be accomplished by any suitable method known in the art, for example, as known in the pharmaceutical field.

A device according to an embodiment of the invention is typically disintegrated and its contents released after a predetermined period, for example after 100 hours or more. Further, a device according to an embodiment of the invention is stopped in a clinically or configurationally abnormal lumen and is disintegrated and its contents released substantially only in a clinically or configurationally abnormal lumen, for example, at the site of a stricture or in a constipated GI tract. Thus, medicaments or markers that are intended to specifically treat or mark strictures of other configurational abnormalities in a body lumen or active agents specifically meant to treat motility abnormalities, such as constipation, can be released, according to embodiments of the invention, in a site specific manner for specific treatment of the abnormality.

According to one embodiment a suspected strictured GI tract may be tested by ingesting a device according to an embodiment of the invention. According to one embodiment the device disintegrates after a period of 12 or 24 hours. A patient suffering from an acutely strictured intestine may show symptoms 12 or 24 hours after ingesting the device bolus. In this case the patient is typically operated on immediately. The device according to an embodiment of the invention may comprise a marker such that a strictured site is marked shortly prior to the surgical procedure, directing the surgeon immediately to the site. In yet another embodiment the device may comprise a medicament such that stricture site may receive medical treatment just prior to the surgical procedure It will be appreciated by persons skilled in the art that the present invention is not limited by what has been particularly shown and described herein above Rather the scope of the invention is defined by the claims, which follow:

What is claimed is:

1. A method for indicating transferability of a non-dissolvable target in-vivo device through the gastrointestinal tract, the method comprising:
   ingesting a dissolvable in-vivo device having initial dimensions similar to the dimensions of said non-dissolvable target in-vivo device, said dissolvable in-vivo device comprising:
      a dissolvable body;
      a dissolvable plug affixed to the body, said body and plug defining a closed receptacle;
      an outer coating, which is essentially impermeable to GI tract liquids, enclosing the plug and the body, said coating covering less than the entire plug; and
      a monitoring mechanism;
   inducing the dissolvable in-vivo device to send a signal, including after a predetermined time period, said predetermined time period being longer than the time the target in-vivo device typically takes to pass through a transferable GI tract; and
   determining transferability of the target in-vivo device through the gastrointestinal tract, wherein receiving a signal from said monitoring mechanism after said predetermined time period is an indication of the presence of said dissolvable in-vivo device within the GI tract, which indicates abnormalities in the GI tract, and wherein not receiving a signal from said monitoring mechanism after said predetermined time period is an indication of said dissolvable in-vivo device not being present within the GI tract, which indicates transferability of the target in-vivo device through the GI tract.

2. The method according to claim 1, comprising monitoring said dissolvable in-vivo device.

3. The method according to claim 1, comprising releasing a substance at an abnormality in the GI tract.

4. The method according to claim 3, wherein said abnormality in the GI tract is a stricture.

5. The method according to claim 3, wherein the substance is a medicament.

6. The method according to claim 1, wherein the monitoring mechanism is an electronic ID tag.

7. The method according to claim 1, wherein the outer coating comprises a non-coated portion through which said dissolvable plug is exposed.

8. The method according to claim 1, wherein the monitoring mechanism is a passive device that provides a signal only upon induction by an external inducer.

9. The method according to claim 1, wherein the signal is an acoustic signal, and the monitoring mechanism provides the acoustic signal upon external induction.

10. A system for indicating transferability of a non-dissolvable target in-vivo device through the GI tract, the system comprising:
   a dissolvable in-vivo device comprising:
      a dissolvable body;
      a dissolvable plug affixed to the body, said body and plug defining a closed receptacle;
      an outer coating, which is essentially impermeable to GI tract liquids, enclosing the plug and the body, said coating covering less than the entire plug; and
      a monitoring mechanism,
   said dissolvable in-vivo device having initial dimensions similar to the non-dissolvable target in-vivo device dimensions, wherein, after a predetermined time period, said predetermined time period being longer than the time a target in-vivo device typically takes to pass through a transferable GI tract, the initial dimensions of said dissolvable in-vivo device change to final dimensions that are smaller than the target in-vivo device dimensions; and
   an external inducer for inducing, including after said predetermined time period, said monitoring mechanism to send a signal;
   wherein receiving a signal from said monitoring mechanism after said predetermined time period is an indication of the presence of said dissolvable in-vivo device within the GI tract, which indicates abnormalities in the GI tract, and wherein not receiving a signal from said monitoring mechanism after said predetermined time period is an indication of said dissolvable in-vivo device not being resent within the GI tract which indicates transferability of the target in-vivo device through the GI tract.

11. The system according to claim 10, wherein said dissolvable in-vivo device further comprises a substance enclosed within the closed receptacle.

12. The system according to claim 11, wherein said substance is a medicament.

13. The system according to claim 10, wherein the monitoring mechanism is an electronic ID tag.

14. The system according to claim 10, wherein the monitoring mechanism is a passive device that provides a signal only upon induction by the external inducer.

15. The system according to claim 10, wherein said signal is an acoustic signal, and the monitoring mechanism provides the acoustic signal upon induction by the external inducer.

* * * * *